US00PP20748P3

(12) United States Plant Patent
Hooper

(10) Patent No.: US PP20,748 P3
(45) Date of Patent: Feb. 16, 2010

(54) *MAGNOLIA* PLANT NAMED 'GENIE'

(50) Latin Name: *Magnolia soulangeana×lilliflora*
Varietal Denomination: GENIE

(76) Inventor: Vance Hooper, 6 Mahoetahi Road, RD 42, Waitara (NZ) 4656

( * ) Notice: Subject to any disclaimer, the term of this patent is extended or adjusted under 35 U.S.C. 154(b) by 54 days.

(21) Appl. No.: 12/157,128

(22) Filed: Jun. 9, 2008

(65) Prior Publication Data

US 2009/0025110 P1 Jan. 22, 2009

(30) Foreign Application Priority Data

Jul. 20, 2007 (NZ) ..... SHM227

(51) Int. Cl.
*A01H 5/00* (2006.01)

(52) U.S. Cl. ..... Plt./223

(58) Field of Classification Search ..... Plt./223
See application file for complete search history.

*Primary Examiner*—Annette H Para

(57) ABSTRACT

A new cultivar of *Magnolia soulangeana×lilliflora* named 'GENIE' that is characterized by fragrant deep rose flowers, rich dark green foliage, and compact size. In combination these traits set 'GENIE' apart from all other existing varieties of *Magnolia soulangeana×lilliflora* known to the inventor.

6 Drawing Sheets

Genus: *Magnolia.*
Species: *soulangeana×lilliflora.*
Denomination: GENIE.

BACKGROUND OF THE INVENTION

This application claims the benefit of priority under 35 U.S.C. 119(f) of the earlier application for New Zealand Plant Breeders Rights, Application Number SHM227 filed Jul. 20, 2007.

The present invention relates to a new and distinct cultivar of Chinese or saucer *magnolia* plant grown as an ornamental for use in the landscape as a specimen tree. The new cultivar is known botanically as *Magnolia soulangeana×lilliflora* and will be referred to hereinafter by the cultivar name 'GENIE'.

'GENIE' is the product of a formal breeding program at the breeder's nursery in Waitara, New Zealand. The purpose of the breeding program is to develop smaller growing *magnolias* which are disease resistant and cover a range of flower colors.

'GENIE' is a seedling selection arising from the inventor's controlled cross-pollination of *Magnolia*×'Sweet Valentine' (unpatented) as the male parent and an unnamed seedling of a cross between *Magnolia soulangeana* 'Sweet Simplicity' (unpatented) and *Magnolia lilliflora* 'Nigra' (unpatented). The cross to make 'GENIE' was done in 1998. 'GENIE' was selected in 2002 when it flowered 2 years from seed. 'GENIE' was chosen for its rich red color that is consistent from the start of the flowering season and until the end of the flowering season. The breeding program process which produced 'GENIE' proceeded as follows:

First in 1989, the female parent of 'GENIE' was raised by crossing *Magnolia soulangeana* 'Sweet Simplicity' as the male parent and *Magnolia* 'Nigra' as the female parent. In 1998, pollen from *Magnolia* 'Sweet Valentine' (male parent of 'GENIE') was applied to receptive stigmas of the newly raised unnamed female parent before its flower opened fully. The resulting seed was collected in the fall and then cleaned and stratified for at least 90 days at 2–4 degrees Celsius. Seed was ready to sow approximately 1 whole year from pollination. Seed was sown in a greenhouse and grown for one season. One year old seedlings were planted in the ground at final spacings and grown until they flowered which occurred from 2 years to 10 years from sowing.

The closest varieties known to the inventor are the parent varieties. 'GENIE' is intermediate between the parents. The seed parent is a small clumping bush with elongated flowers like *Magnolia lilliflora* 'Nigra'. The flowers exhibit typical wavy appearance of cultivars of *M. lilliflora* types. 'GENIE' may also be compared with the variety 'Black Tulip' (unpatented). Whereas 'Black Tulip' is a strong growing *magnolia* which develops a tree fairly quickly, has stems which are 1–2 cm thick in the current season's growth, and produces globular flowers, 'GENIE' is an upright large bush or small tree with slender branches up to 1 cm thick and occasionally 2 cm thick on very strong watershoot growths. 'GENIE' grows 2 or 3 times as high as it does wide. Flowers are globular to cup and saucer form and show some waviness in the tepals, but less so than typical forms of *Magnolia lilliflora.*

The inventor first asexually propagated 'GENIE' in 2002 at the inventor's nursery in Waitara, New Zealand by chip budding (grafting) onto seedling understocks of *Magnolia soulangeana* or *Magnolia kobus.* Under careful observation, the inventor has determined that 'GENIE' is stable, uniform, and reproduces true to type in successive generations of asexual propagation.

SUMMARY OF THE INVENTION

The following represent the distinguishing characteristics of the new *Magnolia soulangeana×lilliflora* cultivar 'GENIE'. In combination these traits set 'GENIE' apart from all other existing varieties of *Magnolia* known to the inventor. 'GENIE' has not been tested under all possible conditions and phenotypic differences may be observed with variations in environmental, climatic, and cultural conditions, however, without any variance in genotype.

1. 'GENIE' is compact in size reaching 1.2–1.5 m tall and approximately 0.7 m in width after one year.
2. 'GENIE' exhibits fragrant deep rose flowers that bloom from early spring to early summer or to mid/late summer when conditions are not too dry.
3. 'GENIE' has rich dark green foliage.
4. 'GENIE' is suitable for use as a specimen tree in the landscape.
5. 'GENIE' performs best in moist, free draining fertile soils in full sun for at least half the day.
6. 'GENIE' is hardy to USDA Zone 4.

BRIEF DESCRIPTION OF THE DRAWINGS

The accompanying color drawings illustrate the overall appearance of the new *Magnolia soulangeana×lilliflora* cultivar 'GENIE' showing the colors as true as it is reasonably possible to obtain in colored reproductions of this type. Colors in the drawings may differ from the color values cited in the detailed botanical description, which accurately describe the actual colors of the new variety 'GENIE'.

Figure 1:
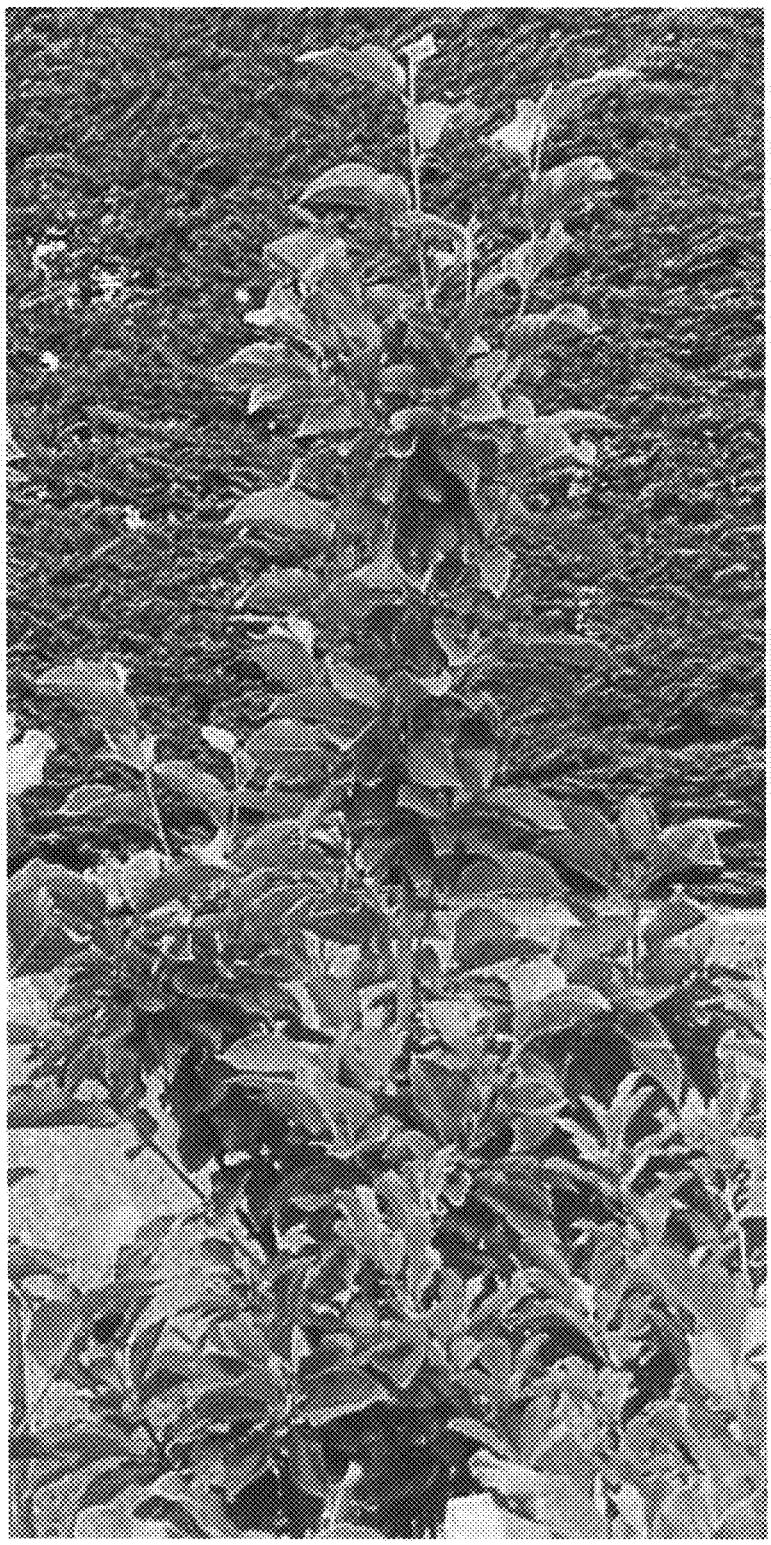
FIG. 1 depicts a 3 year old tree in the summer with flowers in the early stages of bloom.
Figure 2:
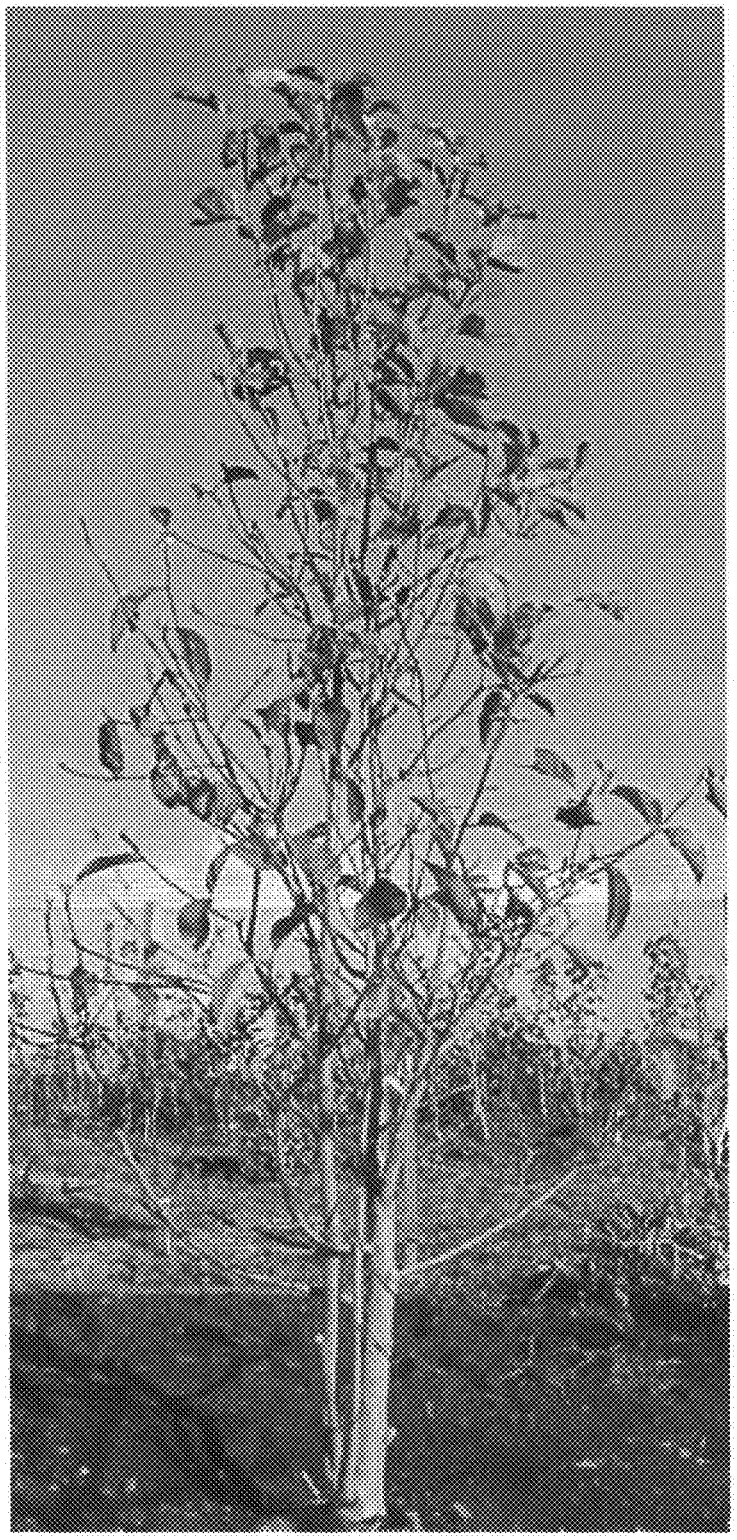
FIG. 2 depicts a 6 year old tree in the fall with foliage dropping showing growth habit.
Figure 3:
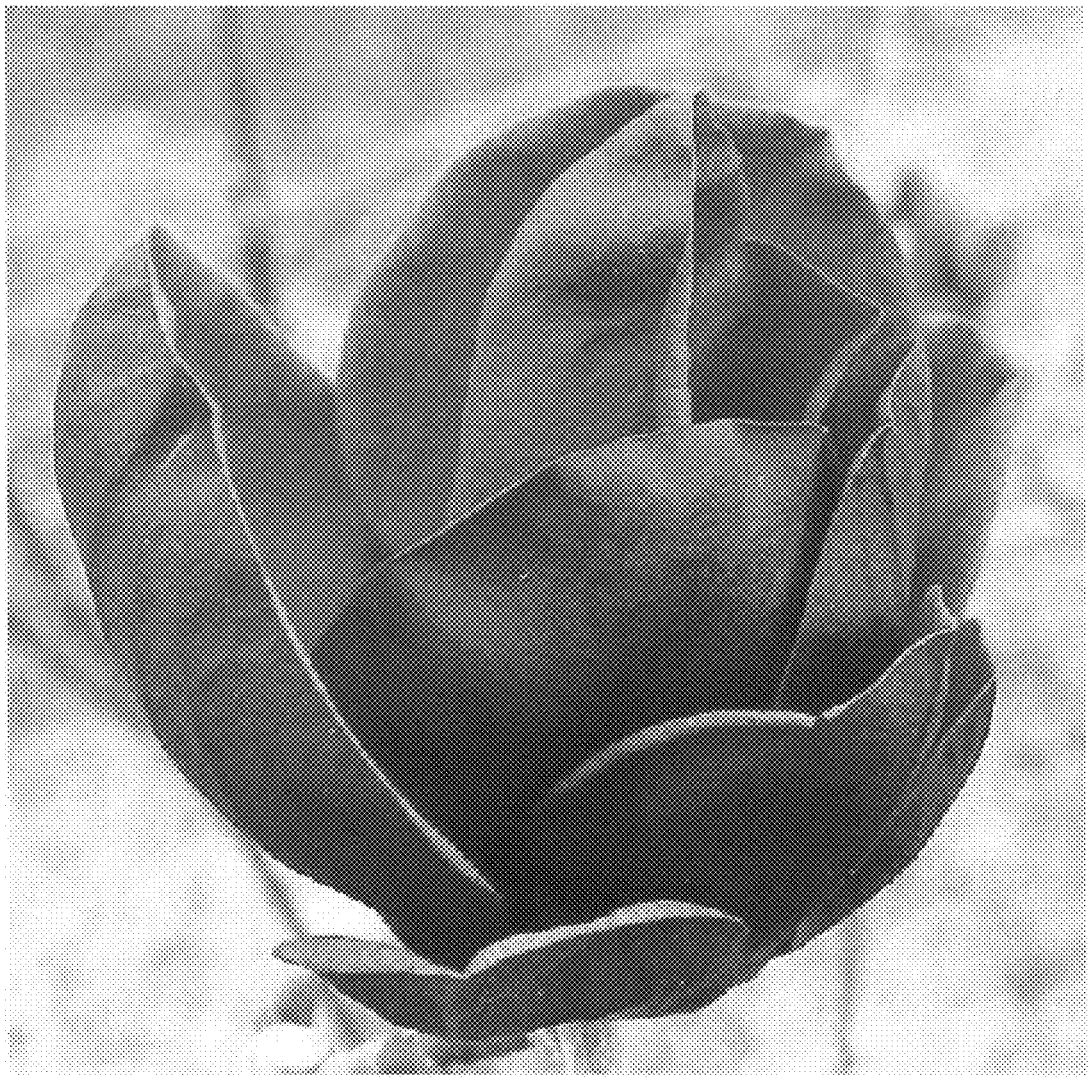
FIG. 3 depicts a newly opened flower in spring before foliage development.
Figure 4:
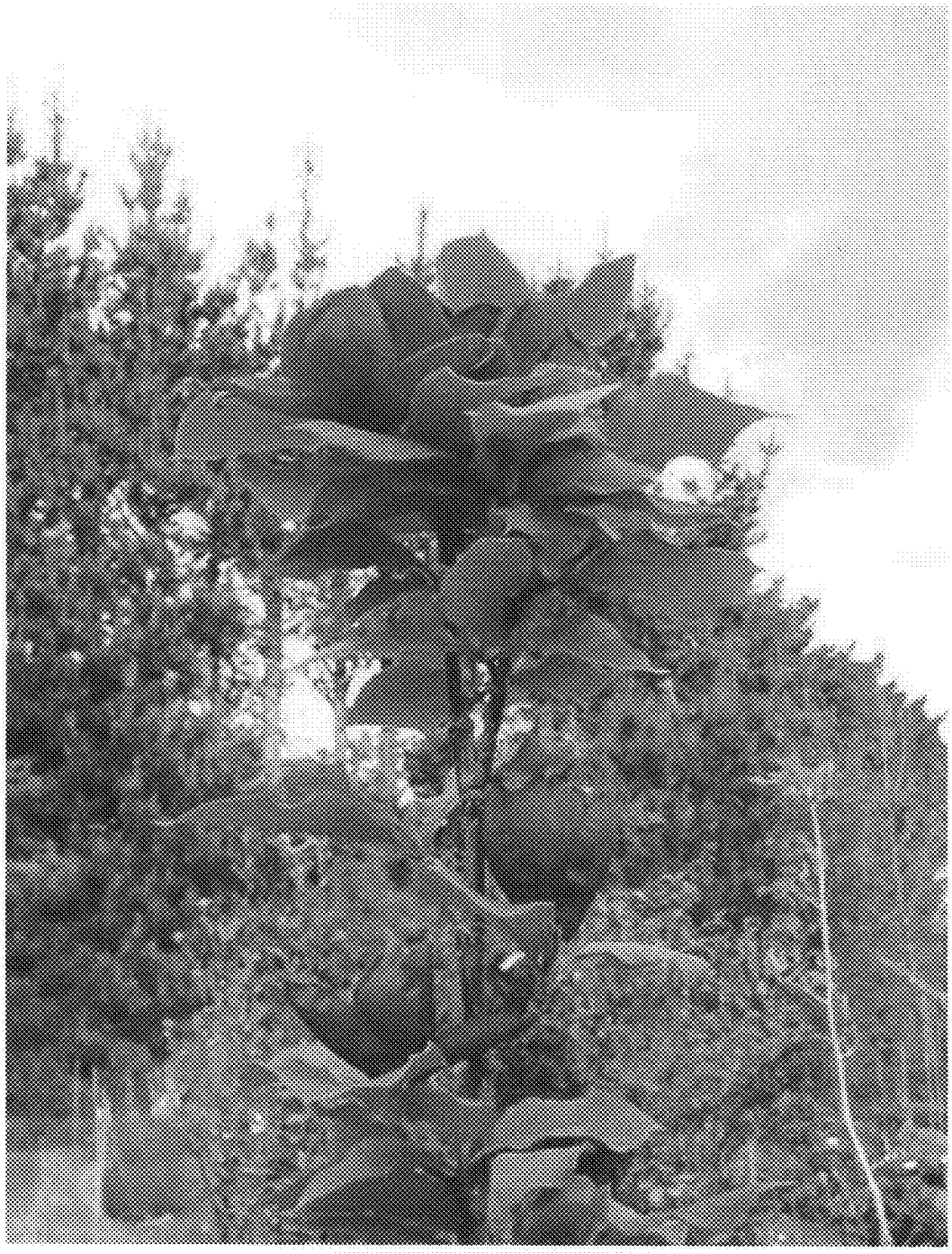
FIG. 4 depicts late spring flowers in various stages of bloom.
Figure 5:
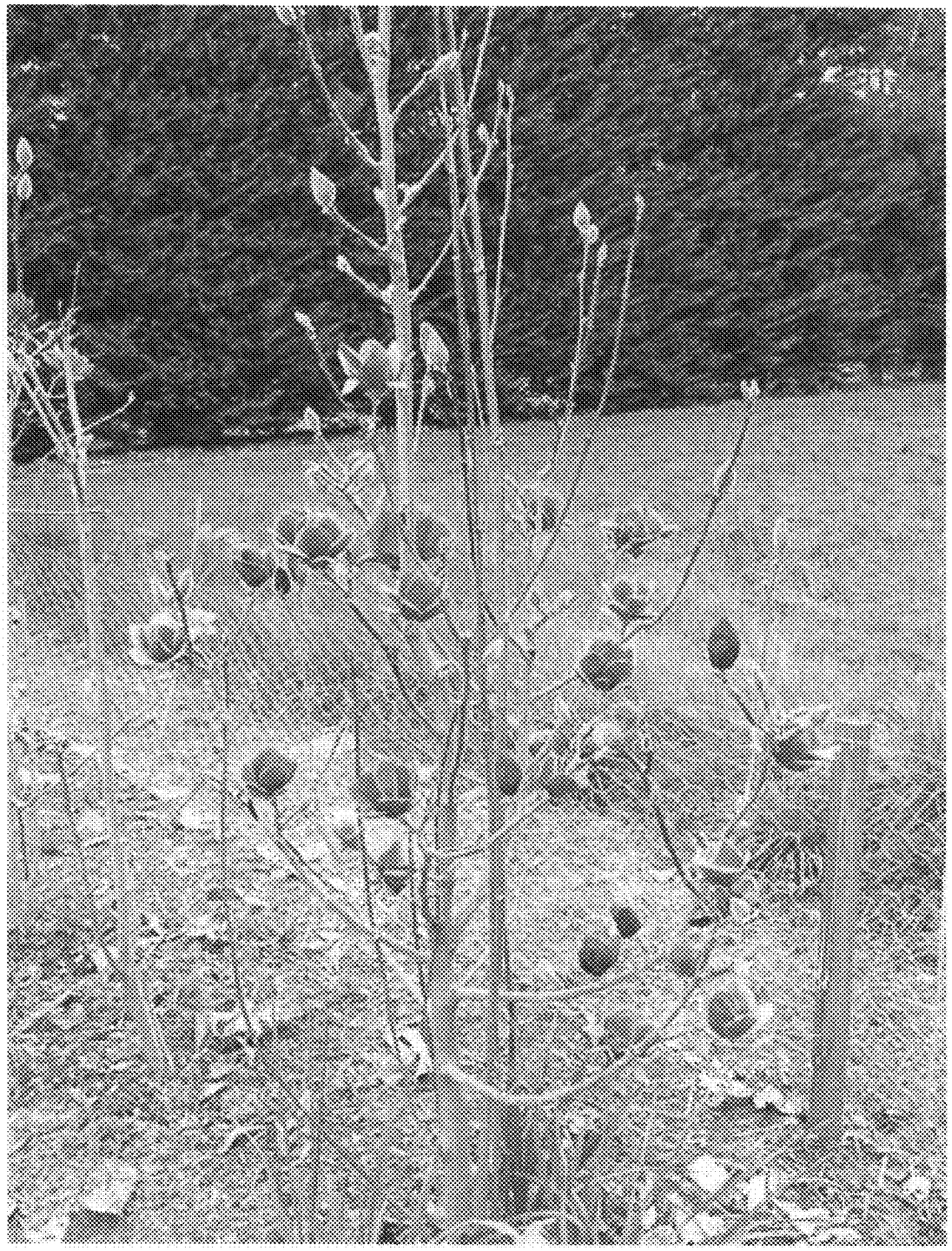
FIG. 5 depicts flowers on a 4 year old tree appearing before the foliage.
Figure 6:
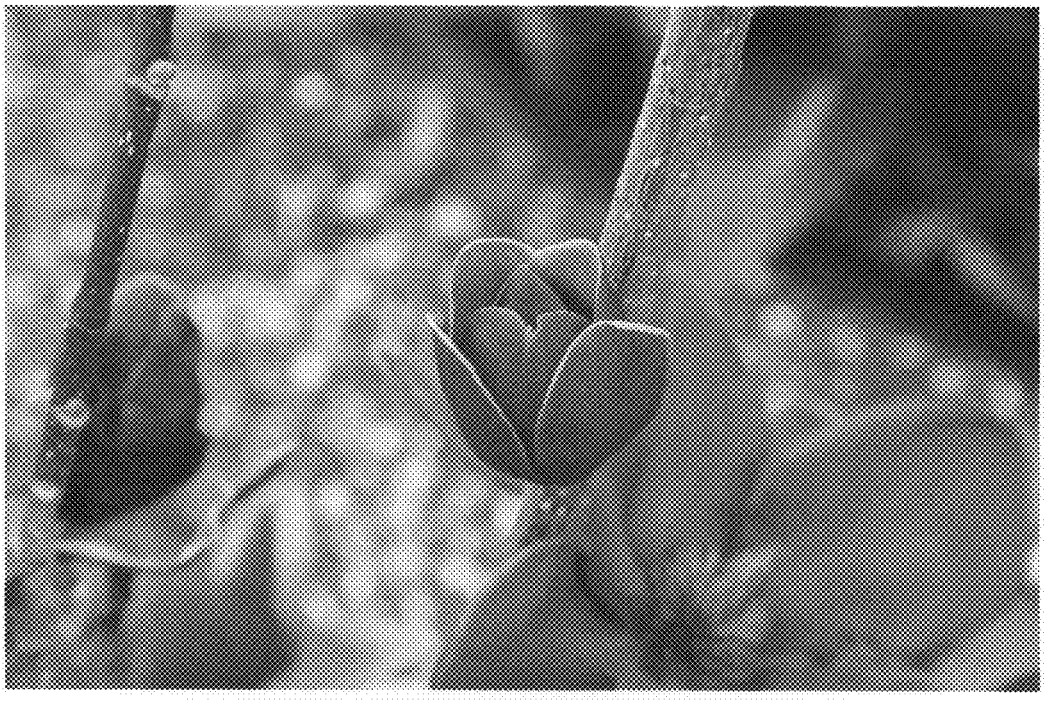
FIG. 6 depicts a flower beginning to open.
Figure 7:
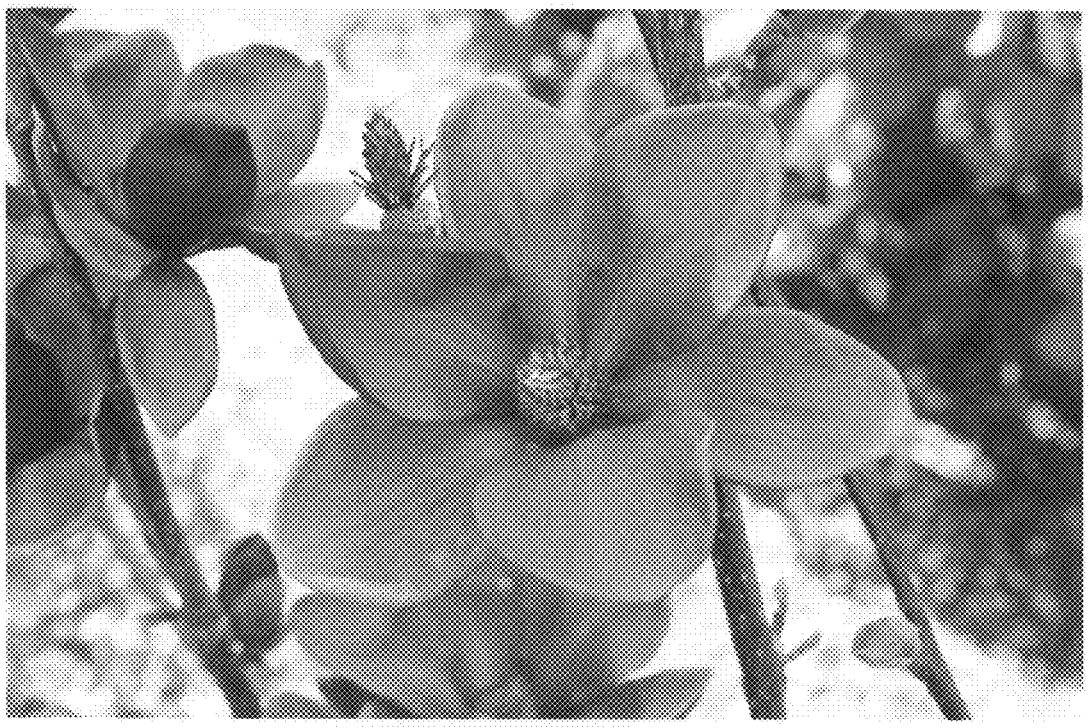
FIG. 7 depicts a flower at the end of its bloom cycle with slightly faded color.

The drawings have been made from photographs taken by conventional techniques and although foliage colors may appear different from actual colors due to light reflectance, they are as accurate as possible by conventional photography.

BOTANICAL DESCRIPTION OF THE PLANT

The following is a detailed description of the *Magnolia soulangeana×lilliflora* cultivar named 'GENIE'. Data was collected in Waitara, New Zealand, from plants grown in the ground out-of-doors in full sun. The plants are approximately 3 years old. Color determinations are in accordance with the 2002 Edition of the Colour Chart of The Royal Horticultural Society, London, England, except where general color terms of ordinary dictionary significance are used. 'GENIE' has not been tested under all possible conditions and phenotypic differences may be observed with variations in environmental, climatic, and cultural conditions, however, without any variance in genotype. The growing requirements are similar to the species.

Botanical classification: *Magnolia soulangeana×lilliflora* 'GENIE'.

Genus: *Magnolia.*

Species: *soulangeana×lilliflora.*

Denomination: 'GENIE'.

Commercial classification: Columnar small tree.

Common name: Chinese *magnolia* or saucer *magnolia.*

Uses: Specimen tree in the landscape.

Container size: Suggested container size is 1.5 to 2 liters for producing a one or two year old plant.

Cultural requirements: Standard conditions for *magnolia* with at least half a day direct sunlight.

Parentage:

*Female parent.*—Breeder's unreleased seedling resulting from *M.×soulangeana* 'Sweet Simplicity' (male parent) and *M. lilliflora* 'Nigra' (female parent).

*Male parent.*—*M.*×'Sweet Valentine'.

Plant description:

*Blooming season.*—Early spring to early summer; to mid to late summer where conditions are moist.

*Plant habit.*—Pyramidal with layers of blooming branches produced each year.

*Vigor.*—Moderate.

*Plant form.*—Columnar small tree.

*Branching.*—Primary branching upward with shorter secondary branching slowly growing sideways.

*Growth rate.*—0.3 m–0.5 m per year.

*Dimensions: (one year from chip budding).*—1.2 m–1.5 m tall and approx. 0.7 m wide.

*Dimensions (anticipated in* 10 *years).*—3.5 m–4 m in height and 1.5 m–2 m in width.

*Hardiness.*—Hardy to USDA Zone 4 with further tests in progress.

*Propagation.*—Softwood cuttings.

*Root system.*—Fibrous.

*Time to initiate roots.*—6 weeks in the summer.

*Time to produce a rooted cutting.*—10 weeks in the summer.

*Crop time.*—First year chip buds reach 1.2–1.5 m tall and approx. 0.7 m wide.

*Seasonal interest.*—Slightly fragrant rose colored flowers from early spring to early/mid/late summer.

*Diseases and pests.*—Resistant to bacterial black spot in New Zealand otherwise not known to be more or less susceptible or resistant to pests or diseases.

*Growing requirements.*—Moist, free draining, fertile soils. Full sun for at least half the day.

Trunk:

*Diameter at ground level (*3 *year old tree).*—3.5 cm–5 cm.

*Bark surface.*—Smooth, becoming furrowed with rough rounded ridges with age.

*Color.*—197A.

*Lenticels.*—Present.

*Lenticel length.*—1 mm.

*Lenticel color.*—199D.

Branches:

*Dimensions.*—35 cm–45 cm in length and 0.7 cm on previous season's growth.

*Internode length.*—5.5 cm.

*Surface texture.*—Smooth.

*Color (immature).*—144A at 2–3 cm from apex, and 146A at least 10 cm from apex.

*Color (mature).*—165A with a glaucous coating giving a grayed appearance.

Foliage description:

*Leaf arrangement.*—Alternate.

*Dimensions.*—10.5 cm–14 cm in length; 10 cm–12 cm in width.

*Shape.*—Oval.

*Apex.*—Obtuse to broadly acuminate.

*Base.*—Rounded.

*Margin.*—Entire, slightly undulated.

*Upper surface.*—Smooth with depressions running on veins. Slightly shiny.

*Lower surface.*—Slightly hairy. Dull green with raised veins.

*Venation pattern.*—Pinnate to reticulate on close examination.

*Color, immature foliage.*—On vigorous shoots 200A covered with a glaucous bloom of fine golden hairs.

*Color, mature foliage.*—Ranges between 147A–139A.

*Venation, immature foliage.*—144A–144B which gradually fill the leaf surface to mature color.

*Venation, mature foliage.*—145A.

*Petiole dimensions.*—12 mm–17 mm in length and 3 mm–6 mm in diameter.

*Petiole color.*—144A covered with fine golden hairs.

Flower description:

*Flower type and habit.*—Globular to bowl shaped, held upright.

*Persistent or self-cleaning.*—Self cleaning.

*Quantity.*—Buds set on all growing tips.

*Natural flowering season.*—Early spring (mid March to late March).

*Age of plants when first flowering.*—Most flower within the first year of growth from budding.

*Flower longevity on the plant.*—7–9 days from shedding of the outer membrane.

*Fragrance.*—Slight.

*Shape.*—Globular opening to bowl shaped with maturity and warmth.

*Diameter.*—15–20 cm diameter when open.

*Depth* (*height*).—8–10 cm from tepal base.

*Flower buds* (*showing color*).—Dimensions: Approximately 3.5 cm in length and 2 cm in width. Shape: Ovate. Color: 187A to 187B.

*Tepals.*—Number: 6–12. Arrangement: Whorled. Dimensions: 5 cm–7 cm in length and 4 cm–4.5 cm in width. Shape: Broadly elliptic. Apex: Acute. Base: Rounded. Margin: Entire. Surface texture: Glabrous. Color (adaxial): 76C when opening progressing to 76A when fully opened. Color (abaxial): 64A when opening progressing to 64B when fully opened.

*Peduncles.*—Dimensions: Approximately 0.5 cm in length and 0.5 cm in diameter. Color: 146C.

Reproductive organs:

*Stamens.*—Quantity: More than 50.

*Filament length.*—1.5 cm–2.5 cm.

*Anther shape.*—Awl shaped.

*Anther dimensions.*—Approximately 0.75 cm in length and approximately 1.1 mm in width.

*Anther color.*—61A at base, 61D fading to white.

*Pollen amount.*—Average to better than average pollen production. Highly fertile when hand pollinating other hybrids.

*Pollen color.*—Pale cream.

*Pistil quantity.*—1.

*Pistil length.*—Approximately 2.2 cm.

*Stigma shape.*—Round.

*Style length.*—Approximately 3 mm.

*Style and ovary color.*—81A.

Seed:

*Quantity per fruiting cone.*—Greater than 50 when hand pollinated, sometimes 2 seeds per follicle.

*Length.*—6 mm–9 mm long on embryo axis and 9 mm–10 mm wide across cotyledons.

*Diameter.*—Seeds flattish, 3 mm–4 mm deep.

*Color.*—Black.

Fruits:

*Type.*—Cone.

*Quantity per tree.*—Very few set without hand pollination. Usually only 2 or 3 seeds produced in open pollinated cones.

*Length.*—8 cm–12 cm.

*Diameter.*—2.5 cm–3.5 cm.

*Texture.*—Smooth with slightly raised lenticels.

*Color.*—Green with whitish lenticels, turning red as seed ripens.

The invention claimed is:

1. A new and distinct variety of *Magnolia* plant named 'GENIE' as described and illustrated.

* * * * *